United States Patent [19]

Effland et al.

[11] Patent Number: 4,868,190
[45] Date of Patent: Sep. 19, 1989

[54] N-PYRIDINYL-9H-CARBAZOL-9-AMINES

[75] Inventors: Richard C. Effland; Joseph T. Klein, both of Bridgewater; Larry Davis, Sergeantsville; Gordon E. Olsen, Somerset, all of N.J.

[73] Assignee: Hoechst-Roussel Pharmaceuticals, Inc., Somerville, N.J.

[21] Appl. No.: 289,887

[22] Filed: Dec. 27, 1988

[51] Int. Cl.$^4$ .................. A61K 31/44; A61K 31/455; C07D 401/12; C07D 401/14
[52] U.S. Cl. ...................... 514/278; 514/337; 546/16; 546/271; 548/440
[58] Field of Search ................... 514/278, 337; 546/16, 546/271; 548/440

[56] References Cited

U.S. PATENT DOCUMENTS 4,752,610 6/1988 Effland et al. ................... 514/343
4,792,562 12/1988 Effland et al. ................... 514/343
4,806,554 2/1989 Effland et al. ................... 514/338

OTHER PUBLICATIONS

Petrow, "J. Chem. Soc.", (1945), pp. 927–928.
Wesseling et al., "New England J. of Medicine", vol. 310, No. 15, pp. 988–989, (1984).
DeLarge et al., "Eur. J. Med. Chem.-Chim Ther.", vol. 15, No. 4, pp. 299–304, (1980).
Miller et al., "J. Med. Chem.", vol. 13, No. 5, pp. 1022–1023, (1980).
Adger et al., "J. Chem. Soc.", Perkin Trans. I, pp. 31–40, (1975).
Arya et al., "Indian J. Chem.", vol. 158, pp. 625–628, (1977).
Khan et al., "J. Chem. Soc.", ©, pp. 86–91, (1970).
Boulton et al., "J. Chem. Soc." Perkin Trans I, pp. 1249–1253, (1986).
Neunhoeffer et al., "Ann. Chem.", pp. 1732–1751, (1985).
Ohsawa et al., "J. Org. Chem.", vol. 50, pp. 5520–5523, (1985).
Koga et al., "Tetrahedron Letters", pp. 1291–1294, (1978).
Clemo et al., "J. Chem. Soc.", (1934), pp. 1739–1741.
Nakajima et al., "J. Org. Chem.", vol. 43, No. 13, pp. 2683–2696, (1978).
Kishimoto et al., "Chem. Pharm. Bull.", vol. 24, No. 12, pp. 3001–3010, (1976).

Primary Examiner—Robert T. Bond
Attorney, Agent, or Firm—Tatsuya Ikeda

[57] ABSTRACT

There are described compounds of the formula:

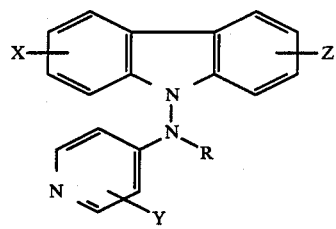

where,
X is hydrogen, loweralkyl, loweralkoxy or halogen;
Y is hydrogen, loweralkyl or halogen;
Z is hydrogen, loweralkyl or halogen;
R is hydrogen, loweralkyl, loweralkenyl, loweralkylcarbonyl, dimethylaminoloweralkyl or

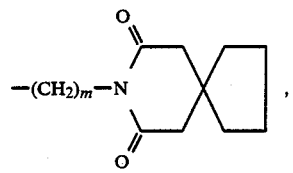

m being an integer of 1 to 6, with the proviso that when R is loweralkenyl the double bond is not alpha to the nitrogen atom;

which compounds are useful analgesic, anticonvulsant and antidepressant agents, and for treating various memory dysfunctions characterized by decreased cholinergic function such as Alzheimer's disease.

22 Claims, No Drawings

N-PYRIDINYL-9H-CARBAZOL-9-AMINES

The present invention relates to novel compounds of the formula:

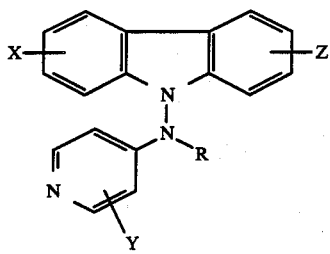

(I)

where,
- X is hydrogen, loweralkyl, loweralkoxy or halogen;
- Y is hydrogen, loweralkyl or halogen;
- Z is hydrogen, loweralkyl or halogen;
- R is hydrogen, loweralkyl, loweralkenyl, loweralkylcarbonyl, dimethylaminoloweralkyl or

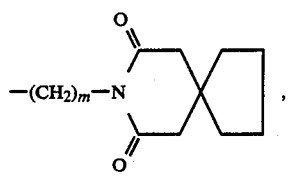

m being an integer of 1 to 6, with the proviso that when R is loweralkenyl the double bond is not alpha to the nitrogen atom;

which compounds are useful analgesic, anticonvulsant and antidepressant agents, and for treating various memory dysfunctions characterized by decreased cholinergic function such as Alzheimer's disease.

Througout the specification and appended claims, a given chemical formula or name shall encompass all stereo, optical, and geometrical isomers thereof where such isomers exist, as wwell as pharmaceutically accetpable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, sec-butyl, t-butyl, and straight- and branched-chain pentyl and hexyl.

Unless otherwise stated or indicated, the term loweralkenyl denotes a straight or branched-chain alkenyl group having from 1 to 6 carbon atoms.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

The compounds of forumula (I) of this invention can be synthesized by following or combining one or more of the steps described below. Throughout the description of the synthetic steps, the definitions of X, Y, Z, R and m are as given above unless otherwise stated or indicated, and other nomenclatures appearing below shall have the same meanings defined in their respective first appearances unless otherwise stated or indicated.

STEP A

A compound of formula (II) where $R_1$ is H or loweralkyl is reacted with a compound of formula (III) to afford a compound of formula (IV).

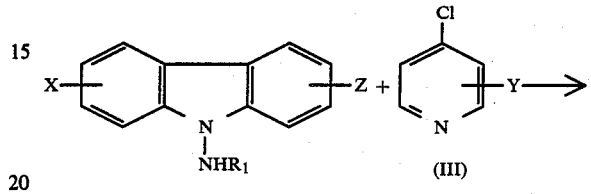

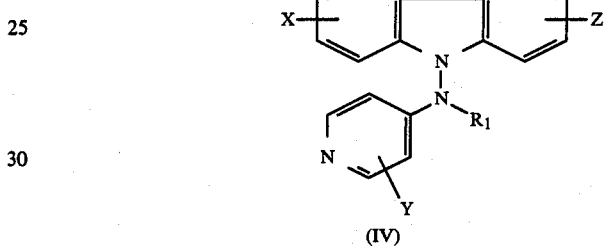

Said reaction is typically conducted in a suitable solvent such as isopropanol or 1-methyl-2- pyrrolidone at a temperature of between about 20° C. and 150° C.

STEP B

A compound of formula IVa obtained from STEP A is treated with a strong base such as sodium hydride or potassium hydride in a suitable solvent such as polar aprotic solvent including dimethylformamide, dimethylsulfoxide and ethereal solvents or aromatic hydrocarbon at a temperature of between about −10 and 50°, preferably 0°−25° to form the anion of IVa, which is reacted with a chloride or bromide compound of the formula $R_2$-W, where $R_2$ is loweralkyl, loweralkenyl, dimethylaminoloweralkyl and W is chlorine or bromine at a temperature of between −10° to 80°, preferably between 0° and 25° to obtain a compound of formula V.

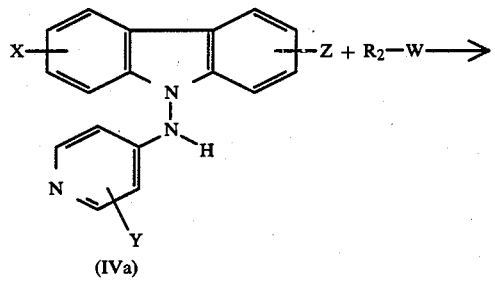

-continued

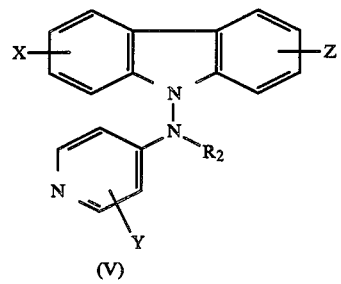

(V)

STEP C

The anion of compund IVa prepared as in STEP B is reacted with a sulfate of the formula $(R_3-O)_2SO_2$ where $R_3$ is loweralkyl, or an O-tosylate of the formula $R_4-O-SO_2C_6H_4CH_3$ where $R_4$ is loweralkyl or

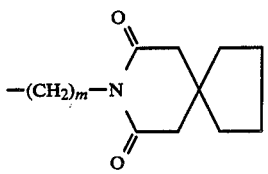

to obtain a compound of the formula VI or VII, respectively.

$(IVa) + NaH + (R_3-O)_2SO_2 \longrightarrow$

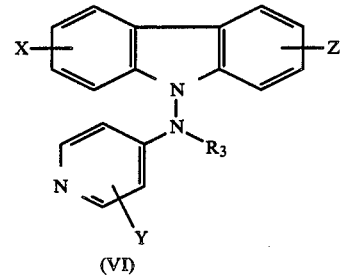

(VI)

$(IVa) + NaH + R_4-O-SO_2C_6H_4CH_3 \longrightarrow$

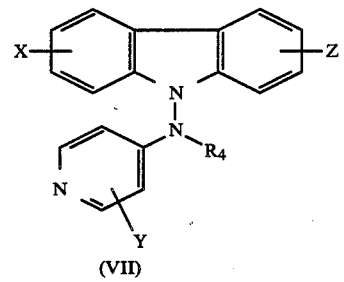

(VII)

The above reaction are conducted typically in a suitable medium such as dimethylformamide at a temperature of about 0° C. to 80° C.

STEP D

Compound IVa is reacted with an alkanoyl chloride of the formula $R_5-CO-Cl$ where $R_5$ is loweralkyl to afford a compound of formula VIII. Said reaction is typically conducted in the presence of an acid scavenger such as sodium bicarbonate in a suitable medium such as dichloromethane at a temperature of 0° C. to 50° C.

$(IVa) + R_5-CO-Cl \longrightarrow$

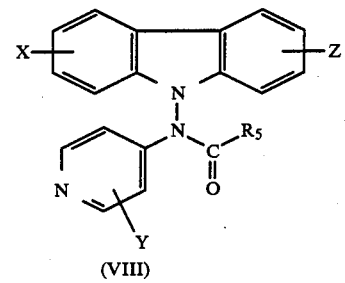

(VIII)

Compounds I of the present invention are useful as analgesic agents due to their ability to alleviate pain in mammals. The activity of the compounds is demonstrated in the 2-phenyl-1,4-benzoquinone-induced writhing (PQW) test in mice, a standard assay for analgesia [Proc. Soc. Exptl. Biol. Med., 95, 729 (1957)] and in modified Haffner's analgesia.

The latter assay is used to evaluate analgesic activity by measuring drug-induced changes in the sensitivty of mice to pressure stress by placing an artery clip (2½ inches long) on their tail. The procedure used is a modification of the test developed by Haffner, Dtsch. Med. Wschr. 55, 731 (1929), and it is described below:

METHOD:

Male mice (Charles River, CD-1) from 18-30 grams are used for the test. An artery clip is applied to the root of the tail of a mouse (approximately ½ inch from the body) to induce pain. The animals quickly responds to this noxious stimuli by biting the clip or the location of the clip. This reaction time, the interval between stimulus onset and response, is recorded on 1/10 second increments by a stop watch.

For a time response, the screening dose (25 mg/kg) is administered subcutaneously (10 ml/kg) to the animal receiving food and water ad libitum before testing. Animals receiving the compound orally are fasted 18-24 hours before drug administration. Drug to be tested is prepared with distilled water and if insoluble, one drop of a surfactant is added.

Twenty-eight animals (seven/group) are administered the drug 15, 30, 45 and 60 minutes prior to testing.

The cut-off time (CO) is determined by taking the ($\bar{x}$) average +3 standard (SD) deviation of the combined response latencies of the control mice in all time periods.

$CO = \bar{x} + 3 \, SD$ (seconds)

Any reaction time, in subsequent drug tests, which is greater than the CO (for the same time period) therefore exceeds 99% of normal Gaussian distribution and is called "positive response" indicative of analgesic activity. A time response indicates the period of greatest analgesic effect after dosing. The $ED_{50}$ is determined at the peak time of drug activity. A minimum of three dose groups are used. $ED_{50}$'s are calcualted using computer analysis.

The results of some of the compounds of this invention are shown in Table 1 along with those of a prior art compound.

TABLE 1
ANALGESIC ACTIVITY

| Compound | PQW (ED$_{50}$, mg/kg, s.c.) | Modified Haffner's Analgesia (ED$_{50}$, mg/kg, s.c.) |
| --- | --- | --- |
| N—(4-pyridinyl)-9H—carbazol-9-amine maleate | 0.5 | 0.4 |
| N—(propyl)-N—(4-pyridinyl)-9H—carbazol-9-amine maleate | 4.3 | 9.8 |
| N—(2-propenyl)-N—(4-pyridinyl)-9H—carbazol-9-amine maleate | 1.0 | 1.2 |
| N—methyl-N—(4-pyridinyl)-9H—carbazol-9-amine maleate | 0.1 | 0.19 |
| N—ethyl-N—(4-pyridinyl)-9H—carbazol-9-amine maleate | 1.1 | 4.3 |
| N—(3-fluoro-4-pyridinyl)-9H—carbazol-9-amine hydrochloride | 1.3 | 0.7 |
| 3-bromo-N—(4-pyridinyl)-9H—carbazol-9-amine maleate | 1.2 | 1.1 |
| (Reference Compound) Pentazocin | 1.3 | 3.9 |

Compounds I of the present invention are also useful as anticonvulsant agents due to their anticonvulsant activity in mammals. Anticonvulsant activity is measured in the male mouse using the supramaximal electroshock (SES) assay described in Arch. Int. Pharmacodyn. 92:97-107, 1952. In this procedure groups of 30 animals are used. Drugs are prepared using distilled water and, if insoluble, a surfactant is added. Control animals receive vehicle. Drugs are routinely administered intraperitoneally (i.p.). The dosage volume is 10 ml/kg. A primary screen is given a 30 minute pretreat. The animal's eyes are placed across the output terminals of an A.C. shocker that delivers 206 volts rms for 300 msec. Electrode paste coats the animals eyes at the point of contact with the terminals. A compound is considered to give protection if the mouse does not exhibit extensor tonus. Protection is expressed as normalized percent inhibition relative to vehicle control.

A time response is carried out using six animals/group. Animals are tested at 30, 60 and 120 minutes postdrug. Additional time periods are tested if indicated by previous tests. When the peak activity time has been determined, a dose response is initiated using 10 animals/group at that time period. The ED$_{50}$ and 95% confidence interval are calculated by computer probit analysis.

TABLE 2
ANTICONVULSANT ACTIVITY

| Compound | ED$_{50}$ (mg/kg,i.p.) |
| --- | --- |
| N—(4-pyridinyl)-9H—carbazol-9-amine maleate | 23.4 |
| N—(propyl)-N—(4-pyridinyl)-9H—carbazol-9-amine maleate | 16.9 |
| N—ethyl-N—(4-pyridinyl)-9H—carbazol-9-amine maleate | 6.4 |
| (Reference Compound) Chlordiazepoxide | 8.0 |

The compounds of formula I of this invention also exhibit antidepressant activities. The antidepressant activities have been evaluated in this invention on the basis of prevention of tetrabenazine-induced ptosis in mice. The test method and results are described below.

Prevention of Tetrabenazine-Induced Ptosis in Mice

Tetrabenazine (TBZ) induces behavioral depression with concomitant ptosis in mice similar to reserpine. Antidepressant compounds, both monoamineoxidase inhibitors and tricyclics, are known to prevent or antagonize these effects and the degree of antagonism correlates with clinical efficacy. The prevention of TBA-induced ptosis in mice is used as a preliminary screen for possible antidepressant activity. The method used in this invention is as follows:

Male mice weighing 20 to 30 grams are used in test groups of five subjects. All compounds are dissolved or suspended with a suitable surfactant in distilled water and administered in volumes of 10 ml/kg of body weight. TBZ solution is made from the methanesulfonate salt and the concentration is adjusted to enable administration of 60 mg/kg of base by intraperitoneal (i.p.) injection.

The pretreatment time is measured from the time of dosing to observation. Therefore, when a 30-minute pretreat is utilized, drug and TBZ are given simultaneously. A control group received solvent and TBZ at intervals identical to drug group. For a primary screen, the drug is administered i.p. and a group size of five is utilized. Eight animals/group are used for a dose range.

Thirty minutes after TBZ, the subjects are placed in individual plastic containers (10.5×8×6 inches) in the presence of white noise and one minute after the transfer, they are scored for ptosis on the following scale: Eyes closed=4, eyes ¾ closed=3, eyes ½ closed=2, eyes ¼ closed=1, eyes open=0. The total score for each group of five in a primary screen will, therefore, be from 0 to 20 and these scores are used as indications of drug activity.

The vehicle control group score is used as a determinant of the validity of each test. If the control scores is less than 17, the results are discarded and the test repeated. The calculation of percent inhibition of ptosis is:

$$\frac{(\text{Control Score} - \text{Drug Score}) \times 100\%}{\text{Control Score}}$$

For ED$_{50}$ estimation, four or five doses are administered in order to bracket the estimated value and only vehicle control socres of 27 to 32 are accepted to assure the accuracy of the ED$_{50}$ estimation.

Linear regression analysis is used to estimate ED$_{50}$ values and 95% confidence intervals.

The results of some of the compounds of this invention are shown in Table 3 along with a result for desipramine (reference compound).

TABLE 3
ANTIDEPRESSANT ACTIVITY

| Compound | ED$_{50}$ (mg/kg, p.o.) |
| --- | --- |
| N—(4-pyridinyl)-9H—carbazol-9-amine maleate | 2.3 |
| N—(propyl)-N—(4-pyridinyl)-9H—carbazol-9-amine maleate | 1.5 |
| N—(2-propenyl)-N—(4-pyridinyl)-9H—carbazol-9-amine maleate | 3.7 |
| N—methyl-N—(4-pyridinyl)-9H—carbazol-9-amine maleate | 1.5 |
| N—ethyl-N—(4-pyridinyl)-9H—carbazol-9-amine maleate | 2.2 |
| N—(butyl)-N—(4-pyridinyl)-9H—carbazol-9-amine hydrochloride | 5.2 |
| 3-bromo-N—(4-pyridinyl)-9H—carbazol-9-amine maleate | 7.6 |
| (Reference Compound) | 2.3 |

TABLE 3-continued
ANTIDEPRESSANT ACTIVITY

| Compound | ED$_{50}$ (mg/kg, p.o.) |
| --- | --- |
| Desipramine | |

Compounds I of the present invention are also useful for the treatment of various memory dysfunctions characterized by decreased cholinergic function such as Alzheimer's disease.

This utility is demonstrated by the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval befoe re-entry into the dark compartment.

The reults for an active compound are expressed as the percent of a group of animals in which the effect of scopolamine is blocked, as manifested by an increased interval between being placed in the test chamber and re-entering the dark compartment.

Test results of scopolamine-induced dark avoidance assay of some of the representative compounds of this invention are presented in Table 4 along with that of a reference compound.

TABLE 4
DARK AVOIDANCE ASSAY

| Compound | Dose mg/kg body weight | % of animals with scopolamine induced memory deficit reversal |
| --- | --- | --- |
| N—(propyl)-N—(4-pyridinyl)-9H—carbazol-9-amine maleate | 2.5 | 33% |
| N—(butyl)-N—(4-pyridinyl)-9H—carbazol-9-amine hydrochloride | 0.63 | 33% |
| N—(3-fluoro-4-pyridinyl)-N—propyl-9H—carbazol-9-amine | 1.25 | 27% |
| 8-[4-(9H—carbazol-9-yl-4-pyridinylamino)butyl]-8-azaspiro[4.5]decane-7,9-dione | 5.0 | 60% |
| 3-bromo-N—(4-pyridinyl)-9H—carbazol-9-amine maleate | 0.31 | 33% |
| Physostigmine (Reference) | 0.31 | 20% |

Effective quantities of the compounds of this invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac or other enteric coating agents. A syrup may contain, in addition to the active compounds, sucrose as a sweetening agent and certain perservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbc acid or sodium bisulfite; chelating agents such as ethylenediaminetetraacetic acid; buffers such as acetates, citates or phosphates and agents for the adjustment of tonicity such as sodium chloride or dextrose. The parenteral preparations can be enclosed in disposable syringes or multiple dose vials made of glass or plastic.

Examples of the compounds of this invention include: N-(4-Pyridinyl)-9H-carbazol-9-amine;

N-Methyl-N-(4-pyridinyl)-9H-carbazol-9-amine;
N-Ethyl-N-(4-pyridinyl)-9H-carbazol-9-amine;
N-(Propyl)-N-(4-pyridinyl)-9H-carbazol-9-amine;
N-(2-Propenyl)-N-(4-pyridinyl)-9H-carbazol-9-amine;
N-(Butyl)-N-(4-pyridinyl)-9-carbazol-9-amine;
N-Dimethylaminopropyl-N-(4-pyridinyl)-9H-carbazol-9-amine;
8-[4-(9H-carbazol-9-yl-4-pyridinylamino)butyl]-8-azaspiro[4.5]decane-7,9-dione;
N-(9H-Carbazol-9-yl)-N-(4-pyridinyl)-propanamide;
N-(3-Fluoro-4-pyridinyl)-9H-carbazole-9-amine;
N-(3-Fluoro-4-pyridinyl)-N-propyl-9H-carbazol-9-amine;
3-Bromo-N-(4-pyridinyl)-9H-carbazol-9-amine; and
3-Bromo-N-propyl-N-(4-pyridinyl)-9H-carbazol-9-amine.

EXAMPLE 1

N-(4-Pyridinyl)-9H-carbazol-9-amine maleate

A solution of 9H-carbazol-9-amine[1] (4.3 g) and 4-chloropyridine hydrochloride (4 g) in 100 ml isopropanol was stirred at reflux for 1.5 hours, and thereafter the mixture was cooled, stirred with ice-water, basified with sodium carbonate and extracted with ethyl acetate. The orgaic extract was washed with water and saturated sodium chloride solution, dried (anhy. MgSO$_4$), filtered and concentrated to 17 g oil. This was purified by flash chromatography (silica, ethyl acetate) to give 5.2 g solid, m.p. 163°–167°. This was converted to the maleate salt in ethanol/ether to yield 5.3 g solid, d 163°–167°. A 3 g portion was recrystallized from methanol/ether to give 2.5 g white crystals, d 165°–167°.

[1]This compound can be prepared, for instance, by reacting carbazole with hydroxylamine-O-sulfonic acid in the presence of milled KOH in a suitable medium such as dimethylformamide (DMF) at ice temperature.

ANALYSIS: Calculated for $C_{17}H_{13}N_3.C_4H_4O_4$: 67.19% C; 4.57% H; 11.19% N. Found: 66.97% C; 4.51% H; 11.11% N.

EXAMPLE 2

N-Methyl-N-(4-pyridinyl)-9H-carbazol-9-amine maleate

To a suspension of NaH which had been prepared by washing 0.68 g of 60% NaH dispersion in oil with hexanes and suspending the solid in 20 ml of DMF and maintained at ice bath temperature was added a solution of N-(4-pyridinyl)-9H-carbazol-9-amine (3.5 g) in 30 ml DMF. The mixture was stirred at ice bath temperature for 15 minutes, and then a solution prepared from 1.59 ml of dimethyl sulfate and 10 ml of DMF was added dropwise. The reaction was allowed to proceed for one hour at ice bath temperature. The mixture was then poured into water and extracted with ethyl acetate. The organic layer was washed with water and dried (sat. NaCl, anhy. MgSO$_4$).

After filtration, the solvent was evaporated to yield a brown oil (3.6 g), which was eluted with ethyl acetate on a silica gel column via HPLC (high pressure liquid chromatography). The desired fractions were concentrated to yield a yellow oil (2.56 g). This material was dissolved in methanol and acidified with maleic acid. After dilution with ether, the resulting precipitate was collected to yield 2.0 g of a white solid, m.p. 125°–127° C.

ANALYSIS: Calculated for $C_{18}H_{15}N_3.C_4H_4O_4$: 67.86% C; 4.92% H; 10.79% N. Found: 67.70% C; 4.83% H; 10.74% N.

EXAMPLE 3

N-Ethyl-N-(4-pyridinyl)-9H-carbazol-9-amine maleate

To a suspension of NaH which had been prepared by washing 0.58 g of 60% NaH dispersions in oil with hexanes and suspending the solid in 20 ml of DMF and maintained at ice bath temperature was added a solution of N-(4-pyridinyl)-9H-carbazol-9-amine (3.0 g) in 30 ml DMF dropwise. This was stirred for 15 minutes and then a solution of diethyl sulfate (2.22 g) in 10 ml DMF was adeed dropwise and the reaction allowed to proceed for 3 hours. The mixture was poured into water and extracted with ethyl acetate. The organic layer was washed with water and dried (sat. NaCl, anhy. MgSO$_4$).

After filtration, the solvent was evaporated to yield an oil (3.55 g) which was eluted with ethyl acetate on a silica gel column via HPLC. The desired fractions were concentrated to yield a yellow oil (3.2 g). This oil was dissolved in methanol and acidified with a methanol solution of maleic acid. After dilution with ether, the resulting precipitate was collected to yield 2.0 g of a off-white solid, m.p. 124°–127° C.

ANALYSIS: Calculated for $C_{19}H_{17}N_3.C_4H_4O_4$: 68.47% C; 5.25% H; 10.42;1 % N. Found: 68.42% C; 5.28% H; 10.39% N.

EXAMPLE 4

N-(Propyl)-N-(4-pyridinyl)-9H-carbazol-9-amine maleate

A solution of N-(4-pyridinyl)-9H-carbazol-9-amine (4 g) in 20 ml dimethylformamide was slowly added to an ice-cooled suspension of sodium hydride which had been prepared by washing 0.8 g of 60% NaH dispersion in oil with hexanes and suspending the solid in 5 ml of dimethylformamide. After the anion formation (15 minutes), a solution of 1-bromopropane (2.4 g) in 5 ml dimethylformamide was added. After one hour, the reaction mixture was stirred with ice/water and extracted with dichloromethane. The organic extract was wshed with water and saturated sodium chloride solution, dried (anhy. MgSO$_4$), filtered and concentrated to 5 g of an oil. This was purified by flash chromatography (silica, ethyl acetate) to give 4.2 g of a solid, m.p. 100°–105°. This was converted to the maleate salt and recrystallized twice from methanol/ether to give 4 g of white crystals, d 174°–175°.

ANALYSIS: Calculated for $C_{20}H_{19}N_3.C_4H_4O_4$: 69.05% C; 5.55% H; 10.07% N. Found: 68.92% C; 5.55% H; 10.06% N.

EXAMPLE 5

N-(2-Propenyl)-N-(4-pyridinyl)-9H-carbazol-9-amine

To a suspension of NaH which had been prepared by washing 0.68 g of 60% NaH dispersion in oil with hexanes and suspending the solid in 20 ml DMF and cooled to ice bath temperature was added N-(4-pyridinyl)-9H-carbazol-9-amine (3.5 g) in 30 ml DMF dropwise. Stirring was continued for 15 minutes at ice bath temperature and then a solution of allyl bromide (1.45 ml) in 10 ml DMF was added dropwise. This mixture was stirred for two hours at ice bath temperature. The mixture was then poured into water and extracted with ethyl acetate. The organic layer was washed with water and dried (sat. NaCl, anhy. MgSO$_4$).

After filtration, the solvent was evaporated to yield a brown oil (4.78 g) which was eluted with ethyl acetate on a silica gel column via HPLC. The desired fractions were concentrated to yield a pale yellow solid (3.0 g). This material was dissolved in ethyl acetate and acidified with an ethyl acetate solution of maleic acid. The resulting precipitate was collected to yield 3.8 g of a white solid, m.p. 158°–160° C.

ANALYSIS: Calculated for $C_{20}H_{17}N_3 \cdot C_4H_4O_4$: 69.39% C; 5.10% H; 10.11% N. Found: 69.31% C; 5.09% H; 10.09% N.

EXAMPLE 6

N-(Butyl)-N-(4-pyridinyl)-9H-carbazol-9-amine hydrochloride

A solution of N-(4-pyridinyl)-9H-carbazol-9-amine (4.2 g) in 20 ml dimethylformamide was added to an ice-cooled suspension of sodium hydride which had been prepared by washing 0.8 g of 60% NaH dispersion in oil with hexanes and suspending the solid in DMF. After the anion formation (15 minutes), a solution of 1-bromobutane (2.7 g) in 5 ml dimethylformamide was added. After stirring at room temperature for two hours, the reaction mixture was stirred with ice/water and extracted with ethyl acetate. The organic extract was washed with water and saturated sodium chloride, dried (anhy. $MgSO_4$), filtered and concentrated to 6 g of an oil. This oil was purified by flash chromatography (silica, ethyl acetate) to give 4.2 g of a solid. The solid was converted to the hydrochloride salt and recrystallized from methanol/ether to give 3.4 g white crystals, d 270°–272°.

ANALYSIS: Calculated for $C_{21}H_{21}N_3 \cdot HCl$: 71.68% C; 6.30% H; 11.94% N. Found: 71.75% C; 6.26% H; 11.94% N.

EXAMPLE 7

N-Dimethylaminopropyl-N-(4-pyridinyl)-9H-carbazol-9-amine

To a suspension of NaH, which had been prepared by washing 0.88 g of 60% NaH dispersion in oil with hexanes, and suspending the solid in 30 ml of DMF and maintained at ice bath temperature was added a solution of N-(4-pyridinyl)-9H-carbazol-9-amine (4.7 g) in 60 ml DMF dropwise. This was stirred for 15 minutes and then a solution of dimethylaminopropyl chloride (2.68 g) in 10 ml DMF was added dropwise to the cool mixture. The reaction was allowed to proceed for 20 hours during which the temperature was changed from ice bath to room temperature. The mixture was poured into water and extracted with ethyl acetate. The organic layer was washed with water and dried (sat. NaCl, anhy. $MgSO_4$).

After filtration, the solvent was evaporated to yield a yellow oil (6.54 g) which was eluted with 10% methanol/DCM on a silica gel column via HPLC. The desired fractions were concentrated to yield a yellow oil which solidified on standing to yield 3.5 g of product, m.p. 71°–74° C.

ANALYSIS: Calculated for $C_{22}H_{24}N_4$: 76.71% C; 7.02% H; 16.26% N. Found: 76.47% C; 7.10% H; 16.26% N.

EXAMPLE 8

8-[4-(9H-carbazol-9-yl-4-pyridinylamino)butyl]-8-azaspiro[4.5]decane-7,9-dione

A solution of N-(4-pyridinyl)-9H-carbazol-9-amine (3 g) in 20 ml dimethylformamide was added to a suspension of sodium hydride which had been prepared by washing 0.6 g of 60% NaH dispersion in oil with hexanes and suspending the solid in 5 ml of DMF. After the anion formation, a solution of 1-(4-hydroxybutyl)-spiro[cyclopentane-1',4-glutarimide]-O-tosylate (5.4 g) in 20 ml dimethylformamide was added. Stirring was continued for twenty hours at ambient temperature, and thereafter the reaction mixture was stirred with water and extracted with ethyl acetate. The organic extract was washed with water and saturated sodium chloride solution, dried (anhy. $MgSO_4$), filtered and concentrated to 8 g of an oil. This oil was purified by flash chromatography (silica, ethyl acetate) to give 5.5 g of a waxy solid. This was recrystallized twice from ethanol to give 3.4 g white crystals, m.p. 90°–92°.

ANALYSIS: Calculated for $C_{30}H_{32}N_4O_2$: 74.97% C; 6.71% H; 11.66% N. Found: 74.64% C; 6.84% H; 11.52% N.

EXAMPLE 9

N-(9H-Carbazol-9-yl)-N-(4-pyridinyl)-propanamide hydrochloride

To a solution of N-(4-pyridinyl)-9H-carbazol-9-amine (5 g) in 200 ml dichloromethane containing sodium bicarbonate (5 g) was added a solution of propionyl chloride (2.2 g) in 20 ml dichloromethane. After two hours, the reaction mixture was stirred with water and extracted with dichloromethane. The organic extract was washed with water and saturated sodium chloride solution, dried (anhy. $MgSO_4$), filtered and concentrated to 8 g of a waxy solid. This solid was purified by flash chromatography (silica, 7% ethyl acetate in dichloromethane) to give 3.5 g of a white solid, m.p. 155°–158°. This solid was converted to the hydrochloride salt in methanol/ether to give 3.0 g white crystals, m.p. 228°–229°.

ANALYSIS: Calculated for $C_{20}H_{17}N_3O \cdot HCl$: 68.28% C; 5.16% H; 11.94% N. Found: 68.61% C; 5.11% H; 11.98% N.

EXAMPLE 10

N-(3-Fluoro-4-pyridinyl)-9H-carbazol-9-amine hydrochloride

To 100 ml isopropanol were added 9H-carbazol-9-amine (8.7 g, 83% pure) and 4-chloro-3-fluoropyridine hydrochloride (8.0 g) and the resulting mixture was stirred at 90° C. for six hours.

The mixture was poured into 500 ml water, stirred for ten minutes, and filtered. The aqueous acidic filtrate was adjusted to pH 10 with $Na_2CO_3$ solution, and extracted with ethyl acetate. The organic layer was washed with water, and dried (saturated NaCl, anhydrous $MgSO_4$).

After filtration, the solvent was evaporated to yield a brown oil (10 g) which was eluted on a silica gel column with 5% ethyl acetate/DCM via HPLC. The desired fractions were combined and concentrated to a tan solid, 5.0 g, m.p. 90° C. A 2.4 g sample of this solid was dissolved in ether, the pH was adjusted to 1 with ethereal HCl, and the resultant tan precipitate was collected and dried to give 2.3 g of product, m.p. >250° C.

ANALYSIS: Calculatd for $C_{17}H_{12}FN_3 \cdot HCl$: 65.08% C; 4.18% H; 13.39% N. Found: 64.73% C; 4.36% H; 13.07% N.

EXAMPLE 11

N-(3-Fluoro-4-pyridinyl)-N-propyl-9H-carbazol-9-amine

To 100 ml isopropanol were added 9H-carbazol-9-amine (4.8 g) and 4-chloro-3-fluoropyridine hydrochloride (4.0 g). The reaction mixture was stirred at 90° C. for six hours, and thereafter poured into 200 ml water, stirred for ten minutes, and filtered. The aqueous acidic filtrate was adjusted to pH 10 with $Na_2CO_3$ solution and extracted with ether. The ether solution was washed with water and dried (saturated NaCl, anhydrous $MgSO_4$).

After filration, the solvent was evaporated to yield 3.0 g of a tan solid which was the intermediate secondary amine.

To a suspension of NaH which had been prepared by washing 0.5 g of 60% NaH dispersion in oil with hexanes and suspending the solid in 10 ml of dry DMF and maintained at 0° C., was added a solution of N-(3-fluoro-4-pyridinyl)-9H-carbazol-9-amine (3.0 g) in 30 ml dry DMF. The mixture was stirred at 0° C. for ten minutes, and thereafter a solution of 1-bromopropane (1.4 ml) in 10 Ml DMF was added, and the mixture was allowed to warm up to ambient temperature.

The mixture was poured into 200 ml ice/water, stirred for five minutes, and extracted with ether. The ether solution was washed with water and dried (saturated NaCl, anhydrous $MgSO_4$).

After filtration, the solvent was evaporated to obtain 3.7 g of a tan solid, which was eluted on a silica gel column with 5% ethyl acetate/DCM via HPLC. The desired fractions were combined and concentrated to yield 2.4 g of a tan solid, m.p. 104°-107° C.

ANALYSIS: Calculated for $C_{20}H_{18}FN_3$: 75.21% C; 5.68% H; 13.16% N. Found: 75.14% C; 5.71% H; 13.05% N.

EXAMPLE 12

3-Bromo-N-(4-pyridinyl)-9H-carbazol-9-amine maleate

To 1-methyl-2-pyrrolidinone was added 3-bromo-9H-carbazol-9-amine (6.8 g) and the reaction mixture heated to 100° C. Then 4-chloropyridine hydrochloride (6.0 g) was added portionwise to the hot mixture and the reaction mixture stirred for 3 hours. The mixture was cooled, poured into water, and basified with a $Na_2CO_3$ solution. The aqueous mixture was then extracted with ethyl acetate, washed with water and dried (saturated NaCl, anhy. $MgSO_4$).

After filtration, the solvent was evaporated to yield a thin brown oil (11.35 g), which was eluted with ethyl acetate on a silica gel column via HPLC. The desired fractions were concentrated to yield an off-white solid (6.1 g). This material was eluted with 5% methanol/DCM on a silica gel column via HPLC. The desired fractions were concentrated to yield a yellow oil (2.7 g). This material was dissolved in methanol and acidified with a methanol solution of maleic acid. After dilution with ether, the resulting precipitate was collected to yield 1.8 g of an off-white solid, m.p. 175°-176° C.

ANALYSIS: Calculated for $C_{17}H_{12}BrN_3 \cdot C_4H_4O_4$: 55.52% C; 3.55% H; 9.25% N. Found: 55.77% C; 3.34% H; 9.11% N.

EXAMPLE 13

3-Bromo-N-propyl-N-(4-pyridinyl)-9H-carbazol-9-amine maleate

To a suspension of NaH (0.5 g) in 10 ml DMF at ice bath temperature was added dropwise a solution of 3-bromo-N-(4-pyridinyl)-9H-carbazol-9-amine (3.5 g), in 40 ml DMF. This was stirred at ice bath temperature for five minutes and then a solution of 1-bromopropane (1.09 ml) in 10 ml DMF was added. The reaction mixture was stirred at ice bath temperature for one hour. The mixture was then poured into water and extracted with ethyl acetate. The organic layer was washed with water and dried (saturated NaCl, anhy. $MgSO_4$).

After filtration, the solvent was evaporated to yield a yellow oil (4.2 g), which was eluted with ethyl acetate on a silica gel column via HPLC. The desired fractions were concentrated to yield yellow oil (3.5 g) which was dissolved in methanol and acidified with a methanol solution of maleic acid. The resulting precipitate was collected to yield 3.05 g of a white solid, m.p. 197°-198° C.

ANALYSIS: Calculated for $C_{20}H_{18}BrN_3 \cdot C_4H_4O_4$: 58.08% C; 4.47% H; 8.47% N. Found: 58.40% C; 4.45% H; 8.43% N.

We claim:

1. A compound of the formula

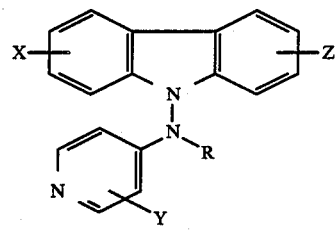

where,
X is hydrogen, loweralkyl, loweralkoxy or halogen;
Y is hydrogen, loweralkyl or halogen;
Z is hydrogen, loweralkyl or halogen;
R is hydrogen, loweralkyl, loweralkenyl, loweralkylcarbonyl, dimethylaminoloweralkyl or

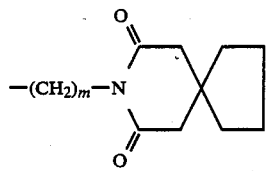

m being an integer of 1 to 6, with the proviso that when R is loweralkenyl the double bond is not alpha to the nitrogen atom;
or a pharmaceutically acceptable acid addition salt thereof.

2. The compound as defined in claim 1, where X is hydrogen or halogen.

3. The compound as defined in claim 1, where Y is hydrogen or halogen.

4. The compound as defined in claim 1, where X is hydrogen or halogen and Y is hydrogen or halogen.

5. The compound as defined in claim 1, which is N-(4-pyridinyl)-9H-carbazol-9-amine.

6. The compound as defined in claim 1, which is N-methyl-N-(4-pyridinyl)-9H-carbazol-9-amine.

7. The compound as defined in claim 1, which is N-ethyl-N-(4-pyridinyl)-9H-carbazol-9-amine.

8. The compound as defined in claim 1, which is N-propyl-N-(4-pyridinyl)-9H-carbazol-9-amine.

9. The compound as defined in claim 1, which is N-(2-propenyl)-N-(4-pyridinyl)-9H-carbazol-9-amine.

10. The compound as defined in claim 1, which is N-butyl-N-(4-pyridinyl)-9H-carbazol-9-amine.

11. The compound as defined in claim 1, which is N-dimethylaminopropyl-N-(4-pyridinyl)-9H-carbazol-9-amine.

12. The compound as defined in claim 1, which is 8-[4-(9H-carbazol-9-yl-4-pyridinylamino)butyl]-8-azaspiro[4.5]decane-7,9-dione.

13. The compound as defined in claim 1, which is N-(9H-carbazol-9-yl)-N-(4-pyridinyl)-propanamide.

14. The compound as defined in claim 1, which is N-(3-fluoro-4-pyridinyl)-9H-carbazol-9-amine.

15. The compound as defined in claim 1, which is N-(3-fluoro-4-pyridinyl)-N-propyl-9H-carbazol-9-amine.

16. The compound as defined in claim 1, which is 3-bromo-N-(4-pyridinyl)-9H-carbazol-9-amine.

17. The compound as defined in claim 1, which is 3-bromo-N-propyl-N-(4-pyridinyl)-9H-carbazol-9-amine.

18. A method of treating a patient in need of relief from pain which comprises administering to such a patient an effective pain alleviating amount of a compound as defined in claim 1.

19. A method of treating a patient in need of relief from convulsion which comprises administering to such a patient an effective convulsion alleviating amount of a compound as defined in claim 1.

20. A method of treating a patient in need of relief from depression which comprises administering to such a patient an effective depression alleviating amount of a compound as defined in claim 1.

21. A method of treating a patient in need of relief from a memory dysfunction characterized by decreased cholinergic function which comprises administering to such a patient an effective memory dysfunction alleviating amount of a compound as defined in claim 1.

22. A pharmaceutical composition comprising a compound as defined in claim 1 in an amount effective for alleviating pain, convulsion, depression or memory dysfunction characterized by decreased cholinergic function, and a suitable carrier therefor.

* * * * *